United States Patent
Chen et al.

(10) Patent No.: US 7,132,563 B1
(45) Date of Patent: Nov. 7, 2006

(54) CONVENIENT METHOD FOR THE PREPARATION OF NO-CARRIER-ADDED O-(2-[$^{18}$F]FLUOROETHYL)-L-TYROSINE)

(75) Inventors: Jenn Tzong Chen, Taoyuan (TW); Wuu Jyh Lin, Taoyuan (TW); Ai Ren Lo, Taoyuan (TW); Ming Hsin Lee, Taoyuan (TW); Hsin Er Wang, Taoyuan (TW); Shih Yan Wu, Taoyuan (TW); Mao Hsiung Chang, Taoyuan (TW)

(73) Assignee: Institute of Nuclear Energy Research, Teoyuan (TW)

( * ) Notice: Subject to any disclaimer, the term of this patent is extended or adjusted under 35 U.S.C. 154(b) by 0 days.

(21) Appl. No.: 11/162,286

(22) Filed: Sep. 6, 2005

(51) Int. Cl.
*C07C 229/36* (2006.01)
(52) U.S. Cl. .................................... 560/27
(58) Field of Classification Search .................. 560/27
See application file for complete search history.

(56) References Cited

U.S. PATENT DOCUMENTS 6,451,835 B1   9/2002   Dekeyser .................... 514/406

OTHER PUBLICATIONS

Hamacher, et al. Efficient routine production of the 18F-labelled amino acid O-(2-[18F]fluoroethyl)-L-tyrosine. Applied Radiation and Isotopes, 2002, 57, 853-856.*

* cited by examiner

*Primary Examiner*—Kamal A. Saeed
*Assistant Examiner*—Shawquia Young
(74) *Attorney, Agent, or Firm*—PaiPatent & Trademark Law Firm; Chao-Chang David Pai

(57) ABSTRACT

This is a novel method for production of no-carrier-added O-(2-[$^{18}$F]fluoroethyl)-L-Tyrosine, which has been proved a suitable PET (position emission tomography) probe for tumor diagnosis imaging, and the preparation of the title compound starts from precursors with the chemical structures as in Formula 1, wherein $R^1$ is a protective group for the carboxyl functional group, $R^2$ is a protective group for the amino group, and $R^3$ acts as a leaving group, $R^1$ represents an arylalkyl group, $R^2$ represents a carboxyl group, and $R^3$ represents a p-tosyloxy, methane sulfonyloxy or trifluoromethane sulfonyloxy or bromine, and the final purification of the product is using a separation column, which is very convenient for automated synthesis, and the invention uses the precursor with the chemical structures as in Formula 1.

2 Claims, 3 Drawing Sheets

CONVENIENT METHOD FOR THE PREPARATION OF NO-CARRIER-ADDED O-(2-[$^{18}$F]FLUOROETHYL)-L-TYROSINE)

BACKGROUND OF THE INVENTION $^{18}$F-labeled O-(2-[$^{18}$F]fluoroethyl)-L-Tyrosine is an amino acid tracer, it has been proved as a suitable PET (position emission tomography) probe for tumor diagnosis imaging. Today, 2-[$^{18}$F]Fluoro-2-Deoxy-D-glucose([$^{18}$F] FDG) has been widely used as a PET agent for evaluate tumor diagnosis and treatment through biohemical pathway of glucose metabolism. Increase brain background radiation due to high absorption of [$^{18}$F]FDG in the brain cause diagnosis difficulty of brain tumor; High [$^{18}$F]FDG absorption of inflammation site also cause misjudgment. Brain tumor cells also have high concentration of L-[methyl-$^{11}$C]methionine, but free of diagnosis difficulty and misjudgment as described above; nevertheless, the half-life of L-[methyl-$^{11}$C]methionine is twenty minutes, therefore, attenuation rapidly during delivery with increasing cost even use cyclotron.

The absorption of $^{18}$F-labeled O-(2-[$^{18}$F]fluoroethyl)-L-Tyrosine through biochemical pathway of amino acid metabolism almost the same as $^{11}$C-labeled L-[methyl-$^{11}$C]methionine, the absorption by brain tumor is much lower than [$^{18}$F]FDG and also by inflammation site. Half-life of both [$^{18}$F]FET and [$^{18}$F]FDG are 109 minutes, this will facilitate the delivery between hospitals, and commercialization is possible because of its cost is lower than $^{11}$C-labeled L-[methyl-$^{11}$C]methionine.

The preparation of O-(2-[$^{18}$F]fluoroethyl)-L-Tyrosine was developed by Wester et al. (J. Nucl. Med. 1999; 40:205–212) and Hamacher et al. (Appl. Radiat. Isot. 2002; 57:853–856). However, it is inconvenient by using high performance liquid chromatography (HPLC) for purified product, it is not only cumbersome but also difficult automation, since during HPLC purification process operator must switch valve from waste collecting bottle to product bottle in order to collect purified O-(2-[$^{18}$F]fluoroethyl)-L-Tyrosine and switch valve back to waste bottle after complete the collection of purified product in order to maintain high purified O-(2-[$^{18}$F]fluoroethyl)-L-Tyrosine. This procedure is impotent, since bad control of valve will cause loss or impurity product and manufacturer must face with problems of unqualified product and increasing cost of manufacturing equipment.

CITED REFERENCES

H. J. Wester, M. Herz, W. Weber, P. Heiss, R. Senekowitsch-Schmidtke, M. Schwaiger and G. Stöcklin, Synthesis and radiopharmacology of O-(2-[$^{18}$F]fluoroethyl)-L-Tyrosine for tumor imaging. J. Nucl. Med. 40, 205–212 (1999).

K. Hamacher and H. H. Coenen, Efficient routine production of the $^{18}$F-labelled amino acid O-(2-[$^{18}$F]fluoroethyl)-L-Tyrosine, Appl. Radiat. Isot. 57, 853–856 (2002).

SUMMARY OF THE INVENTION

The object of this invention provides a synthetic method of novel t-BOC-(O-tosyloxyethyl)-L-Tyr-OBzl (as Formula 1), which is a precursor of O-(2-[$^{18}$F]fluoroethyl)-L-Tyrosine.

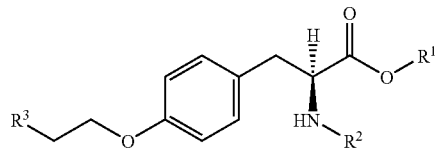

Formula 1: Synthesis Precursors for O-(2-[$^{18}$F]fluoroethyl)-L-Tyrosine.

For the synthesis of O-(2-[$^{18}$F]fluoroethyl)-L-Tyrosine, the initial labeled-compound (that is precursor) is prepared above all. This synthesis procedure is carried out in chemistry lab instead of in radiation control area because of no radiation.

Precursor of O-(2-[$^{18}$F]fluoroethyl)-L-Tyrosine

Synthesis of O-(2-[$^{18}$F]fluoroethyl)-L-Tyrosine: (1) Prepare ethylene glycol-1,2-ditosylate. React ethylene glycol and toluenesulfonyl chloride in pyridine solution at low temperature for two to three days, warming the solution, solidify the product and purify by re-crystallization to obtain ethylene glycol-1,2-ditosylate. (2) Prepare t-Boc-(O-tosyloxyethyl)-L-Tyr-Obzl. Add t-Boc-L-Tyr-OBzl in acrylonitrile solution contains ethylene glycol-1,2-ditosylate and potassium carbonate, heat to 90° C. while stirring the reaction for four hours, remove solvent after complete the reaction, then extract with chloroform to obtain solid residue, purify dissolved residue by column chromatography and obtain pure t-Boc-(O-tosyloxyethyl)-L-Tyr-OBzl product.

Another object of the invention provides a synthetic method of a novel O-(2-[$^{18}$F]fluoroethyl)-L-Tyrosine. It must be carry out in radiation control room or area when use this precursor as an initial labeling substance.

Synthetic method of O-(2-[$^{18}$F]fluoroethyl)-L-Tyrosine comprises:

(1) Use Kryptofix 2.2.2 as a catalyst. Perform substitution reaction of t-Boc-(O-tosyloxyethyl)-L-Tyr-OBzl with $^{18}$F ion in acrylonitrile solution under Kryptofix 2.2.2 catalysis and yield t-Boc-([$^{18}$F]fluoroethyl)-L-Tyr-OBzl, dry after purify by column chromatography, add 1N HCl after resultant resolve in alcohol, hydrolysis at temperature of 100° C., obtain isotonic solution by neutralize with 1N NaOH, then obtain final product after filter by 0.22 μm bacteria-free filtering film.

(2) Use Tetrabutylammonium bicarbonate(TBAHCO$_3$) as a catalyst. Perform substitution reaction of t-Boc-(O-tosyloxyethyl)-L-Tyr-OBzl with $^{18}$F ion in acrylonitrile solution under TBAHCO$_3$ catalysis and yield t-Boc-(O[$^{18}$F]fluoroethyl)-L-Tyr-OBzl, dry after purify by column chromatography, add 1N HCl after resultant resolve in alcohol, hydrolysis at temperature of 100° C., obtain isotonic solution by neutralize with 1N NaOH, then obtain final product after filter by 0.22 μm bacteria-free filtering film.

Precursor used as an initial substance in the invention utilize resin and silica gel column for purification, the smooth synthetic procedure similar the production of [$^{18}$F] FDG, therefore, automation is applicable. It is not necessary use high performance liquid chromatography (HPLC) for purification; the cost of synthetic equipment is lower as well. Experience technician of [$^{18}$F]FDG synthesis in PET-CT center can operate this equipment easily.

The advantage of this invention in nuclear medicine includes: (1) Use $^{18}$F nuclide with 109 minutes half-life as radioactive tracer; it increases reliability of supply for clinical use of PET-CT center in compare to $^{11}$C and the distribution to other medical center is also possible. (2) Utilize resin and silica gel column for purification; the smooth synthetic procedure suitable for automatic production will enhance the convenience and repeatability of synthesis and decrease it production time as well as labor cost. (3) Save manufacturing cost and simplify flow processes without using HPLC equipment, that is, raise the success probability of synthesis and qualification ratio of quality control.

DETAILED DESCRIPTION OF THE INVENTION

Figure 1:
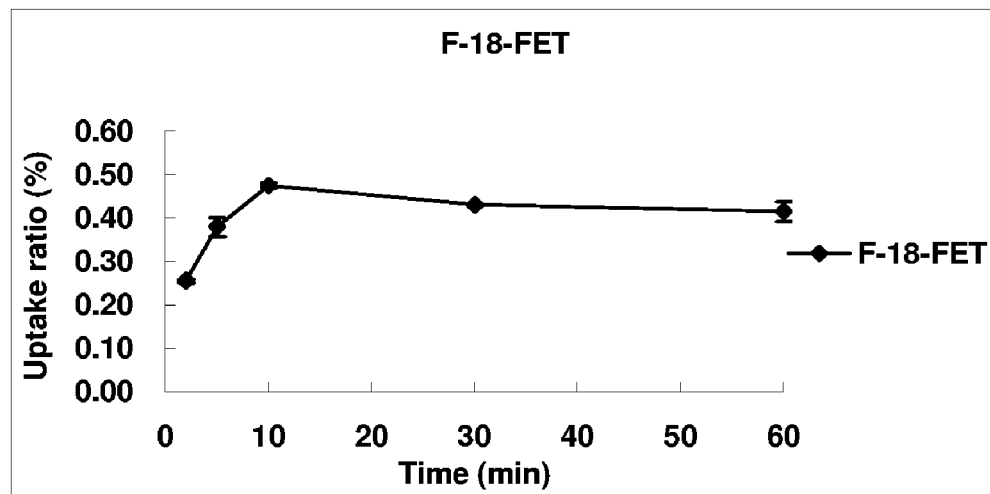
FIG. 1 is the L-[$^{18}$F]FET intake of F98 glioma cells at different time points.

Embodiments of the invention will be described as follows:

Example 1

The Synthetic Method of $^{18}$F-Labeled Precursor t-BOC-(O-tosyloxyethyl)-L-Tyr-OBzl 1. Preparation of ethylene glycol-1,2-ditosylate (1) Add 17 g of toluenesulfonyl chloride (TsCl) (F.W.=190.65, 0.089 mol) into conical flask (A) with 20 ml of pyridine.

(2) Add 1.1 ml of ethylene glycol (F.W.=62.07, 0.018 mol) into conical flask (B) with 30 ml of pyridine.

(3) Pour solution of conical flask (A) into conical flask (B) under the temperature of dry ice-acetone bath (−30° C. approximately) and then put the flask under −18° C. promptly for react two to three days.

(4) After complete reaction, pour the reactant in conical flask (B) into 500 ml beaker with ice water and cracked ice; white solid substance will appear after stirring.

(5) Add optimal 1N HCl into beaker above-mentioned and adjust pH to 6~7.

(6) Filter and collect white solid substance, then re-crystallize in mixture of methylene chloride and normal hexane to yield 80% of 5.33 g ethylene glycol-1,2-ditosylate.

Formula 2: Reaction of Synthetic ethylene glycol-1,2-ditosylate

2. Preparation of t-BOC-(O-tosyloxyethyl)-L-Tyr-OBzl

Following is the synthetic process of using t-BOC-L-Tyr-OBzl as a raw material (Formula 2):

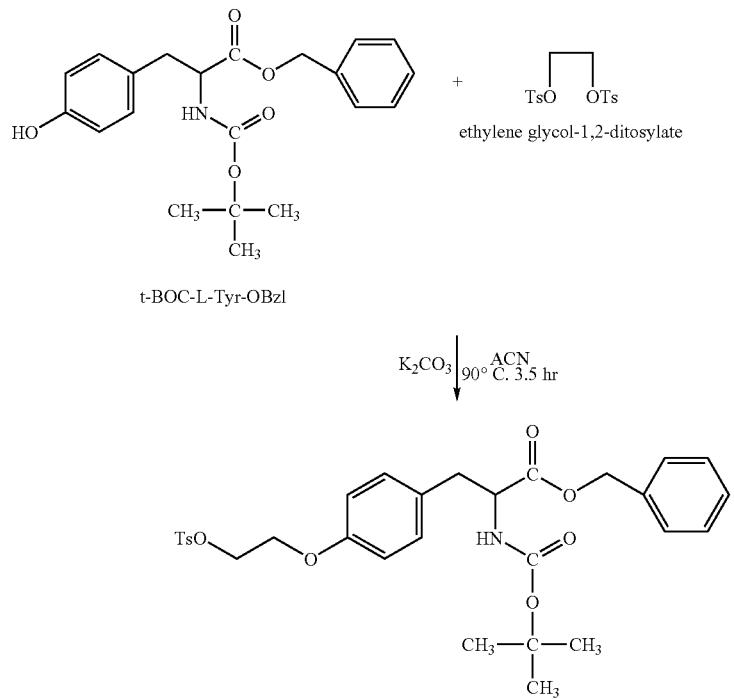

Formula 3: The Synthetic Reaction of t-BOC-(O-tosyloxyethyl)-L-Tyr-OBzl from t-BOC-L-Tyr-OBzl (1) Add 450 mg of N-tert-butyloxycarbonyl-L-tyrosine benzylester (t-BOC-L-Tyr-OBzl) (F.W.=361, 1.24 mmol) into 50 ml of round bottomed flask contains 20 mg potassium carbonate and 1.384 g ethylene glycol-1,2-ditosylate (F.W.=370.35, 3.73 mmol); then add 25 ml anhydrous acetonitrile at 90° C. and stir for 3.5 hours.

(2) After complete the reaction, remove solvent with rotavapor and extract with chloroform (5 ml×3). Harvest chloroform extract and remove solvent under negative pressure.

(3) Dissolve solid residue with minimum amount of methylene chloride, then perform silica gel chromatography (add 0.1% triethylamine in eluent) for purification. The initial condition of mobile phase is 100% $CH_2Cl_2$; after remove un-react ethylene glycol-1,2-ditosylate the condition of mobile phase change to $CH_2Cl_2/CHCl_3=1/1$, the crude product then eluted. Dry crude product under reduced pressure and obtain the solid crude product.

(4) Dissolve crude product with minimum volume solution of $CH_2Cl_2:CHCl_3=8/2$, then perform silica gel chromatography (add 0.1% triethylamine in eluent) for purification; the initial condition of mobile phase is $CH_2Cl_2/CHCl_3=8/2$ (another 0.1% triethyl amine is added); light yellow oil-like substance (398 mg) of pure N-tert-butyloxycarbonyl-(O-tosyloxyethyl)-L-tyrosine benzylester (t-BOC-(O-tosyloxyethyl)-L-Tyr-OBzl) is eluted; re-crystallize in dichloromethane and n-hexane to yield 60.1% of white solid substance, melt point 85~86° C.

(5) Nuclear Magnetic Resonance (NMR): Dissolve 20 mg of t-BOC-(O-tosyloxyethyl)-L-Tyr-OBzl in 0.6 ml $CDCl_3$, then determine its $^1$H-NMR spectrum (Formula 3). $^1$H NMR ($CDCl_3$) δ7.80 (d, 2H, J=8.4 Hz, Haryl), 7.31 (m, 7H, Haryl), 6.89 (d, 2H, J=8.4 Hz, Haryl), 6.62 (d, 2H, J=8.4 Hz, Haryl), 5.15 (d, 1H, 12.2 Hz, CH of benzyl), 5.08 (d, 1H, 12.2 Hz, CH of benzyl), 4.92 (d, 1H, J=8.0 Hz, NH), 4.54 (m, 1H, CH), 4.33 (t, 2H, J=4.6 Hz, $CH_2$), 4.07 (t, 2H, J=4.6 Hz, $CH_2$), 2.99 (d, 2H, J=5.8 Hz, $CH_2$ of Tyr), 2.43 (s, 3H, $CH_3$ of toluene), 1.39 (s, 9H, $CH_3$ of t-BOC).

(6) Elemental analysis: The formula of t-BOC-(O-tosyloxyethyl)-L-Tyr-OBzl is $C_{30}H_{35}NO_8S$, the calculated value of elemental analysis is: C, 63.27; H, 6.15; N, 2.46. The actual value is: C, 63.34; H, 5.62; N, 2.33.

Example 2

Use Kryptofix 2.2.2 as a Catalyst to Produce O-(2-[$^{18}$F]fluoroethyl)-L-Tyrosine

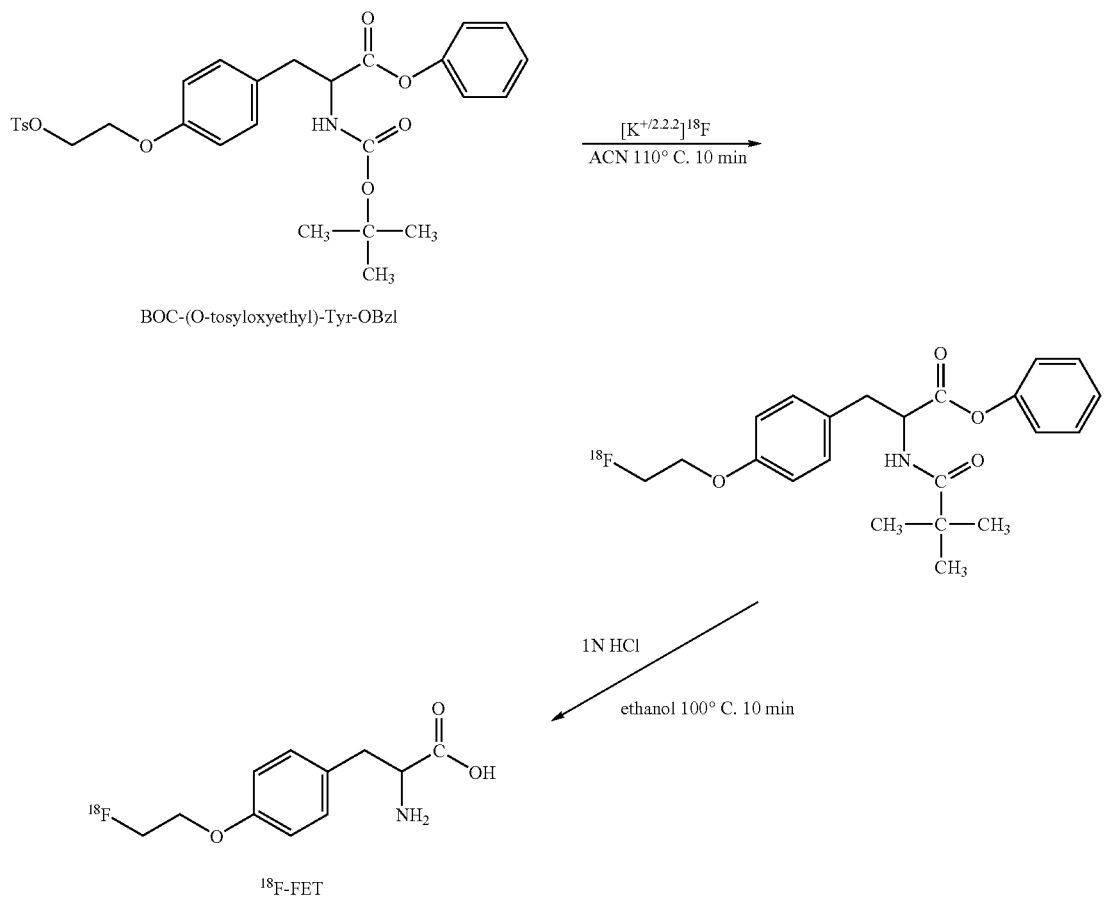

Formula 4: Method of using Kryptofix 222 to produce L-[$^{18}$F]FET (1) Pour [$^{18}$F]HF solution (0.5–1.3 ml, radioactivity 1–500 mCi) into 5 ml pointed-base bottle with potassium carbonate (4.6 mg) and kryptofix 222 (26 mg); heat under 130° C., purge with nitrogen gas (200 ml/min) and vacuum smoothly until the surface of liquid almost dry.

(2) Add slowly 3 ml anhydrous acetonitrile in eight minutes while heat under 130° C.; then purge with nitrogen gas (200 ml/min) and vacuum smoothly so that azeotropic dry moisture and acetonitrile.

(3) Dissolve 5 mg t-BOC-(O-tosyloxyethyl)-L-Tyr-OBzl in 0.8 ml anhydrous acetonitrile, then add into above bottle at 110° C. for 10 mins reaction.

(4) After complete the reaction, insert evacuation needle while maintaining at 110° C. and purge with nitrogen gas (200 ml/min) until dry (take about 5 minutes to eliminate acetonitrile).

(5) Cold the reaction bottle to room temperature, adds 1.5 ml CHCl$_3$ for dissolve reaction mixture and determine its radioactivity. Take a small fraction of solution for thin-layer chromatography (silica gel plate, developing agent CH$_2$Cl$_2$/CHCl$_3$=8/2). Pass above solution through pre-conditioned silica column while increase flow rate by weak hydrogen gas pressure; wash bottle with 1.5 ml CHCl$_3$ before pass through the same silica column and the discarded effluent fluid is collected by waste bottle. Again, use 2.5 ml ether for silica column elution and collect effluent ether solution with capped test tube the primary product having a protective group. Take a small fraction of collected solution for thin-layer chromatography (silica gel plate, developing agent CH$_2$Cl$_2$/CHCl$_3$=8/2). Determine the radioactivity of collected solution, silica column and reaction bottle.

(6) Put capped test tube into 40° C. water bath, purge with nitrogen (200 ml/min) and aspirate slowly until dry. Add 0.3 ml 1N hydrochloride after solids dissolve by 0.3 ml ethanol and put into heating block (100° C.) for ten-minute hydrolytic reaction.

(7) Take out bottle after complete reaction, neutralize with 0.35 ml 1N sodium hydroxide solution and add additional 1.35 ml pure water to constitute a total volume of 2 ml isotonic solution, then cold to room temperature.

(8) Pass product through 0.22 μm bacteria-free filtering film and enter aseptic bottle as to obtain bacteria-free and carrier-free L-[$^{18}$F]FET solution; determine radioactivity of filtered product (yield 30~40%, decay corrected) and analyze radiochemical purity (>90%) by thin-layer chromatography (reverse C18 plate, acetonitrile/10 mM ammonium acetate=7/3).

Example 3

Use tetrabutylammonium bicarbonate CTBA$^+$HCO$_3{}^-$) as a Catalyst to Produce O-(2-[$^{18}$F]fluoroethyl)-L-Tyrosine

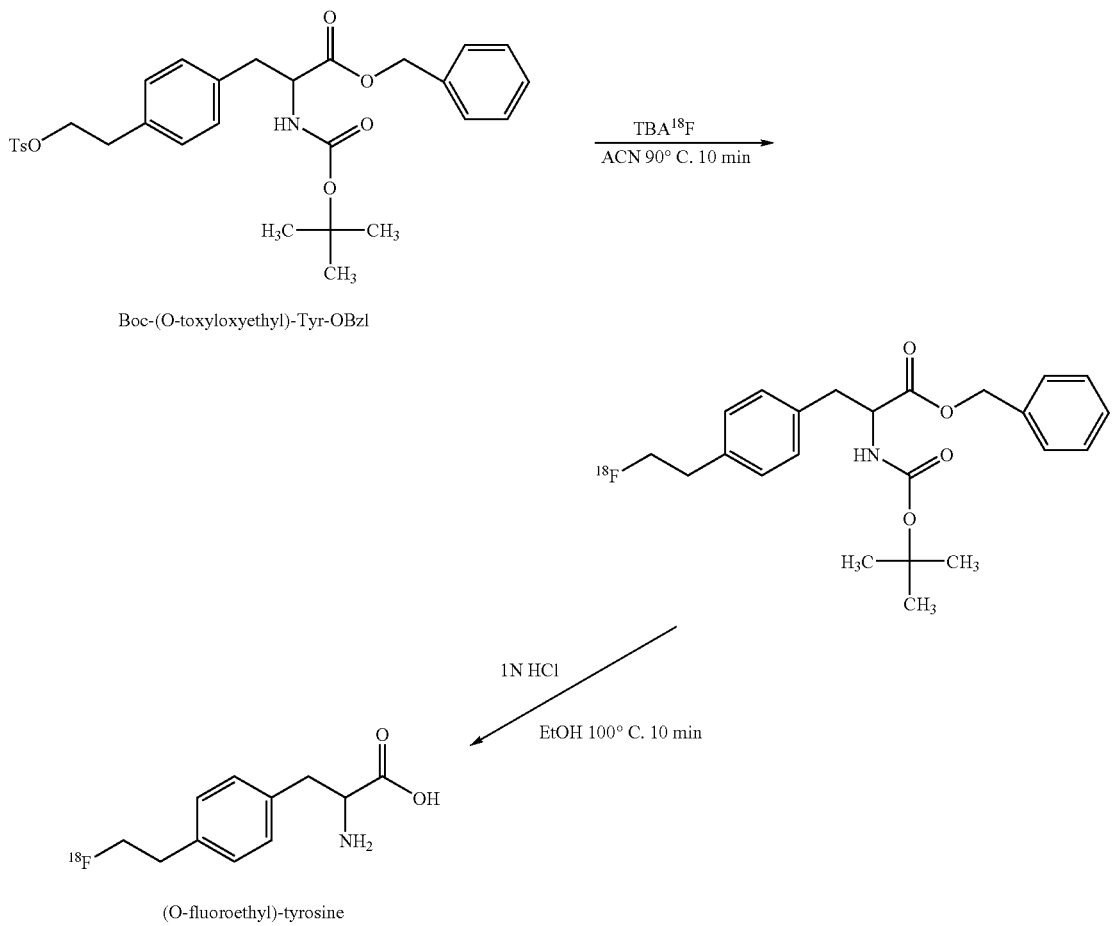

Formula 5: Method of using TBAHCO$_3$ to produce L-[$^{18}$F]FET (1) Determine radioactivity of [$^{18}$F]HF solution. Use peristaltic pump push [$^{18}$F]HF solution through preconditioned QMA Sep-pak (1 ml/min), discard effluent fluid passed QMA (into [$^{18}$O] water-returnable bottle). Determine radioactivity of effluent fluid and QMA Sep-pak.

(2) Elute QMA Sep-pak (1 ml/min) with 0.8 ml TBAHCO$_3$/ACN and collect effluent fluid of TBAHCO$_3$ into pointed-base bottle. Heat the bottle with heating block (100° C.), purge with nitrogen gas (200 ml/min) and vacuum smoothly until the surface of liquid almost dry.

(3) Add 2 ml of anhydrous acetonitrile slowly in eight minutes while heating at 100° C. and purge with nitrogen gas (200 ml/min). Vacuums smoothly so that azeotropic dry moisture and acetonitrile.

(4) Dissolve 5 mg t-BOC-(O-tosyloxyethyl)-L-Tyr-OBzl in 0.8 ml anhydrous acetonitrile, then add into above bottle at 90° C. for react 10 minutes.

(5) After complete the reaction, insert evacuation needle while maintaining at 90° C. and purge with nitrogen gas (200 ml/min) until dry (take about 5 minutes to eliminate acetonitrile).

(6) Cold the reaction bottle to room temperature. Adds 1.5 ml CHCl$_3$ and shakes for dissolve reaction mixture before determine its radioactivity. Take a small fraction of solution for thin-layer chromatography (silica gel plate, developing agent CH$_2$Cl$_2$/CHCl$_3$=8/2). Pass above solution through pre-conditioned silica column while increase flow rate by weak hydrogen gas pressure; wash bottle with 1.5 ml CHCl$_3$ before pass through the same silica column and the discarded effluent fluid is collected by waste bottle. Again, use 2.5 ml ether for silica column elution and collect effluent ether solution with capped test tube to obtain primary product have protective group. Take a small fraction of collected solution for thin-layer chromatography (silica gel plate, developing agent CH$_2$Cl$_2$/CHCl$_3$=8/2). Determine the radioactivity of collected solution, silica column and reaction bottle.

(7) Put capped test tube into 40° C. water bath, purge with nitrogen (200 ml/min) and aspirate slowly until dry. Add 0.3 ml 1N hydrochloride after solids dissolve by 0.3 ml ethanol and put into heating block (100° C.) for ten-minute hydrolytic reaction.

(8) Take out bottle after complete reaction, neutralize with 0.35 ml 1N sodium hydroxide solution and add additional 1.35 ml pure water to constitute a total volume of 2 ml isotonic solution, then cold to room temperature.

(9) Pass product through 0.22 μm bacteria-free filtering film and enter aseptic bottle as to obtain bacteria-free and carrier-free L-[$^{18}$F]FET solution; determine radioactivity of filtered product (yield 40~50%, decay corrected) and analyze radiochemical purity (>90%) by thin-layer chromatography (reverse C18 plate, acetonitrile/10 mM ammonium acetate=7/3).

Example 4

Evaluation of L-[$^{18}$F]FET Uptake by F98 Glioma Tumor Cells (1) In five six-well plates, put 1×10$^6$ F98 glioma cells and 2 ml DMEM (1 g glucose/l) into three wells.

(2) Total of five time points (2, 5, 10, 30 minute and 1 hour) in this experiment and each time point use one six-well plate.

(3) Predetermined activity of L-[$^{18}$F]FET or [$^{18}$F]FDG (10 μCi/well) is added into each well during the experiment. Radioactivity uptake of cells divided by total added radioactivity can obtain its calculated uptake ratio.

(4) Formula 4 shows the result of L-[$^{18}$F]FET intake by F98 glioma cells. F98 glioma cells intake L-[$^{18}$F]FET rapidly and maximal accumulation will reach after 10 minutes (uptake ratio 0.47%). As cell cannot metabolize L-[$^{18}$F]FET, therefore, the rate of L-[$^{18}$F]FET transportation by the cells become balance after ten minutes when add L-[$^{18}$F]FET; the accumulation of L-[$^{18}$F]FET in glioma cells only slightly decrease after 1 hour (uptake ratio 0.41%).

Example 5

Biological Distribution of L-[$^{18}$F]FET in F98 Glioma Cells of Fischer 344 Rat (1) Total of twenty Fischer 344 male rats will be assessed in vivo for L-[$^{18}$F]FET biological distribution. Use the intersection of bregma and sagittal midlines as original point; so as to implant F98 glioma cells (1×10$^5$ cells/10 μl) at the place of 3 mm left 5 mm upward and 5 mm depth. Biological distribution test will be carry out after 11~12 days of brain tumor implantation.

(2) Different volume of radioactive level is injected, injected volume of L-[$^{18}$F]FET for each Fischer 344 rat is 200~300 μl, that is approximately 200~250 μCi of activity.

(3) Inject L-[$^{18}$F]FET via tail vein, and rats are sacrificed at 15, 30, 60, 90 and 120 minutes.

(4) Dissection of rat organ is right after sacrifice. Scissors off chest and abdomen fur alone the line from genital pore upward to jowl. Next, scissors off chest above xiphisternal transversely. Open ribs aside, take blood sample from venous sinus with 0.5 ml syringe. Withdraw the needle after depletion of blood and collect the extracted heart. Collect the lung lobes with forcep.

(5) Scissors off abdominal muscle from genital pore upward to the position below xiphisternal longitudinally. Then, scissors off the opening of upper and lower edges transversely, everts muscle layers to both sides and expose celiac organs. Search for bladder in lower abdomen and sequentially removes stomach, liver, spleen, small intestine, large intestine, kidney, and muscle.

(6) After turn over the rat, scissors off fur of shoulder and removes exposed subcutaneous tumor. Cut scalp upward at lower margin of cranium above foramen magnum and expose cranial bone. Then, cut cervical portion transversely at foramen magnum and expose spinal cord. Inserts foramen magnum with scissors' tip while attach the inner surface of cranium; such that scissors' tip can reach the frontal edge of cranial cavity in order to scissor off the center of cranium. Use scissors to open cranium aside and expose brain tissue. Alone skull base insert scissors deeply to the front edge of cranial cavity in order to remove left-brain, right-brain and brain tumor.

Figure 2:
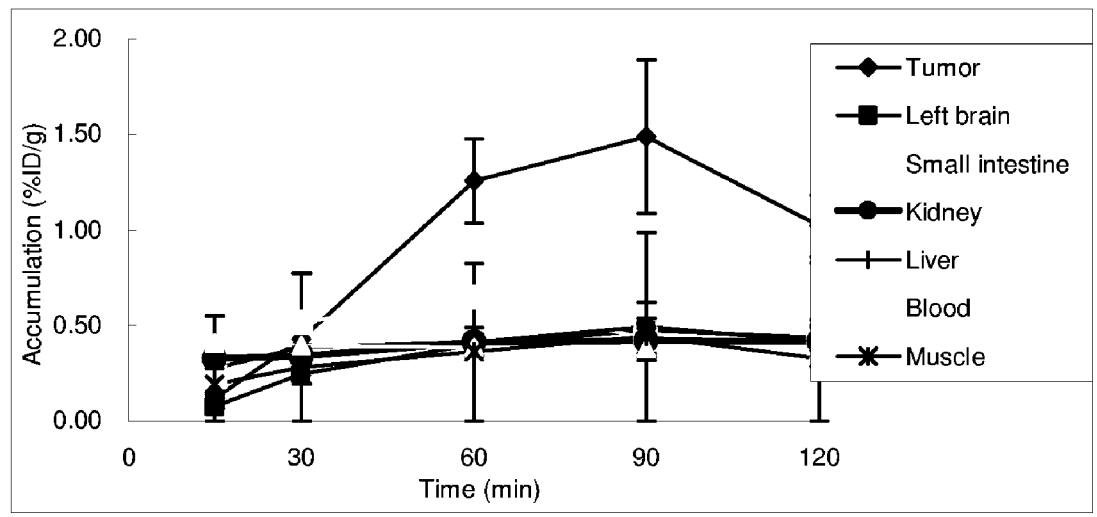
FIG. 2 is the accumulated radioactivity in organs at different time points after injected L-[$^{18}$F]FET into tumor-bearing rat.

(7) Weight all organ samples; measure radioactivity with γ-counter and convert to % ID/g (% injection dose/g organ) of each organ for estimate the biological distribution of L-[$^{18}$F]FET. From the observation of biological distribution find out that radiotracer accumulation of tissue may vary depend on the duration after intake L-[$^{18}$F]FET; the radioactivity of each tissue is expressed by % ID/g (percent injected dose per gram of tissue); the experimental results are showed in table 1 and FIG. 2. According to reports, L-[$^{18}$F]FET can pass through blood brain barrier (BBB) and enter brain by way of L amino acid transporter system. This study result of L-[$^{18}$F]FET biological distribution shows that maximum accumulation of L-[$^{18}$F]FET in brain tumor and normal brain tissue is at 90 minutes, that is 1.49 and 0.48% ID/g respectively. Tumor- to-normal brain ratio of L-[$^{18}$F]FET at 15, 30, 60, 90 and 120 minutes are 1.54, 1.74, 3.16, 3.14 and 2.34 respectively. Besides brain tumor, rat pancreas also accumulate large amount of L-[$^{18}$F]FET (0.98, 1.76, 2.55, 2.28 and 2.24% ID/g respectively at 15, 30, 60, 90 and 120 minutes); the increasing radioactivity of L-[$^{18}$F]FET in pancreas is because of pancreas require large amount of amino acid for synthesis various enzymes and hormones. Some papers reported that patient with tumor observes no significant accumulation of radioactivity in pancreas when use positron emission tomography (PET), the discrepant results were assumed that human and rat have different metabolic pathway. Furthermore, biological distribution study of L-[$^{18}$F]FET indicated radioactivity accumulation in tumor cells (expressed by % ID/g) are much higher than other normal organs (left-brain, small intestine, kidney, liver, blood and muscle) except pancreas, this means L-[$^{18}$F]FET can be a potential PET agent for substantially different site of tumor. Since L-[$^{18}$F]FET is excrete via urine, therefore, high level of radioactivity will be found in urine sample.

TABLE 1

Determination of accumulated radioactivity (% ID/g) in organs at different time points after injected L-[$^{18}$F]FET into tumor-bearing rat

| Organ | 15 min | 30 min | 60 min | 90 min | 120 min |
| --- | --- | --- | --- | --- | --- |
| Blood | 0.41 ± 0.03 | 0.39 ± 0.03 | 0.38 ± 0.00 | 0.37 ± 0.03 | 0.36 ± 0.03 |
| Lung | 0.32 ± 0.05 | 0.43 ± 0.09 | 0.43 ± 0.07 | 0.45 ± 0.02 | 0.40 ± 0.06 |
| Heart | 0.30 ± 0.06 | 0.40 ± 0.07 | 0.43 ± 0.07 | 0.47 ± 0.02 | 0.43 ± 0.07 |
| Stomach | 0.24 ± 0.05 | 0.36 ± 0.06 | 0.40 ± 0.05 | 0.43 ± 0.04 | 0.41 ± 0.03 |
| Liver | 0.27 ± 0.06 | 0.37 ± 0.07 | 0.41 ± 0.06 | 0.49 ± 0.01 | 0.41 ± 0.09 |
| Spleen | 0.31 ± 0.08 | 0.50 ± 0.11 | 0.51 ± 0.09 | 0.48 ± 0.11 | 0.47 ± 0.04 |
| Pancreas | 0.98 ± 0.25 | 1.76 ± 0.16 | 2.55 ± 0.31 | 2.28 ± 0.76 | 2.24 ± 0.72 |
| Small intestine | 0.23 ± 0.11 | 0.52 ± 0.26 | 0.65 ± 0.04 | 0.43 ± 0.11 | 0.41 ± 0.09 |
| Large intestine | 0.21 ± 0.01 | 0.28 ± 0.05 | 0.42 ± 0.06 | 0.46 ± 0.04 | 0.38 ± 0.09 |
| Kidney | 0.33 ± 0.01 | 0.34 ± 0.06 | 0.41 ± 0.08 | 0.42 ± 0.07 | 0.41 ± 0.09 |
| Muscle | 0.19 ± 0.03 | 0.28 ± 0.01 | 0.36 ± 0.04 | 0.44 ± 0.10 | 0.37 ± 0.10 |
| Left brain | 0.08 ± 0.01 | 0.25 ± 0.05 | 0.40 ± 0.06 | 0.48 ± 0.14 | 0.43 ± 0.09 |
| Right brain | 0.07 ± 0.02 | 0.21 ± 0.03 | 0.34 ± 0.03 | 0.48 ± 0.08 | 0.34 ± 0.04 |
| Tumor | 0.12 ± 0.02 | 0.43 ± 0.10 | 1.26 ± 0.22 | 1.49 ± 0.40 | 1.02 ± 0.16 |

Example 6

Positron Emission Tomography (PET) of Tumor-Bearing Rat with L-[$^{18}$F]FET (1) Positron emission tomography (PET) studies of tumor-bearing rat (Fischer 344) with L-[$^{18}$F]FET will be carry out after 11~12 days of brain tumor (F98 glioma) implantation.

(2) Producing processes of L-[$^{18}$F]FET as described above, and estimates its administrating amount of agent according to the level of radioactivity.

(3) At the very beginning, inject 400 μCi of L-[$^{18}$F]FET into tail vein. Temporarily anesthetize rats with ether at time of 0.5, 1, 1.5 and 2 hours. Fix rat on transparent acrylic board and place on PET table after securing stretched limbs on the board. Continuously anesthetize rats with isoflurane gas. Align implant portion of head with PET machine as to assure the fixation of original imaging position.

(4) Adjust background value by blank scan before PET imaging.

(5) Use Ga-68 radioactive source proceed transmission scan for adjust tissue attenuation.

Figure 3:
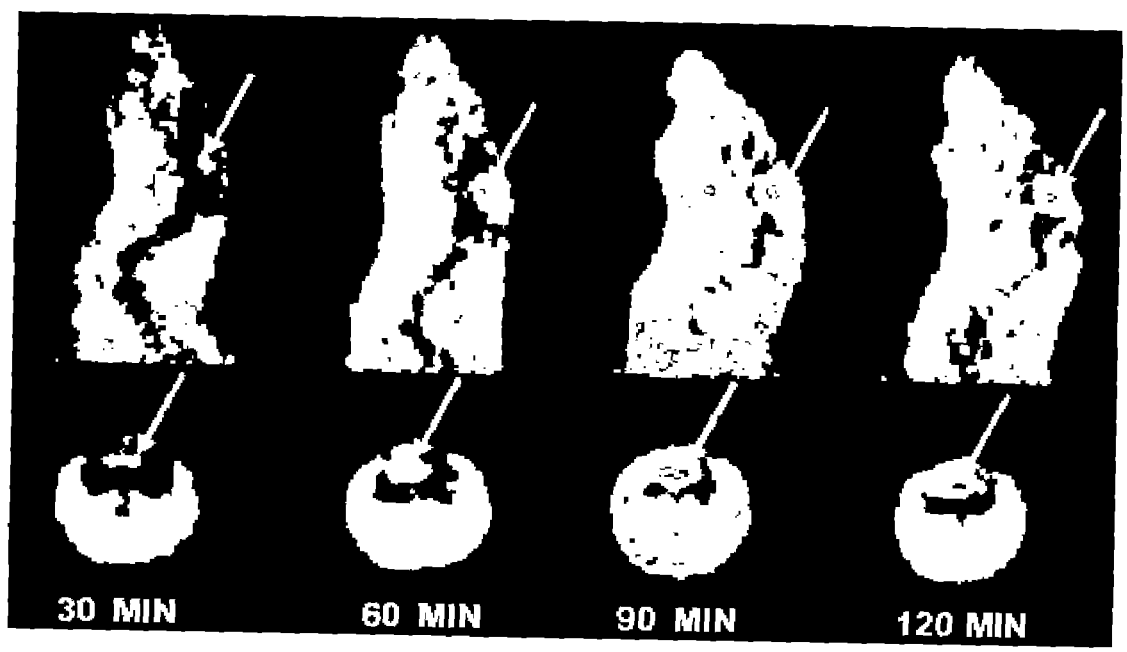
FIG. 3 is the microPET imaging of left-brain F98 rat glioma implanted Fischer344 rat after inject L-[$^{18}$F]FET at 30, 60, 90 and 120 minutes respectively; upper row represent the coronal scan and lower row represent the cross section scan.
Figure 4:
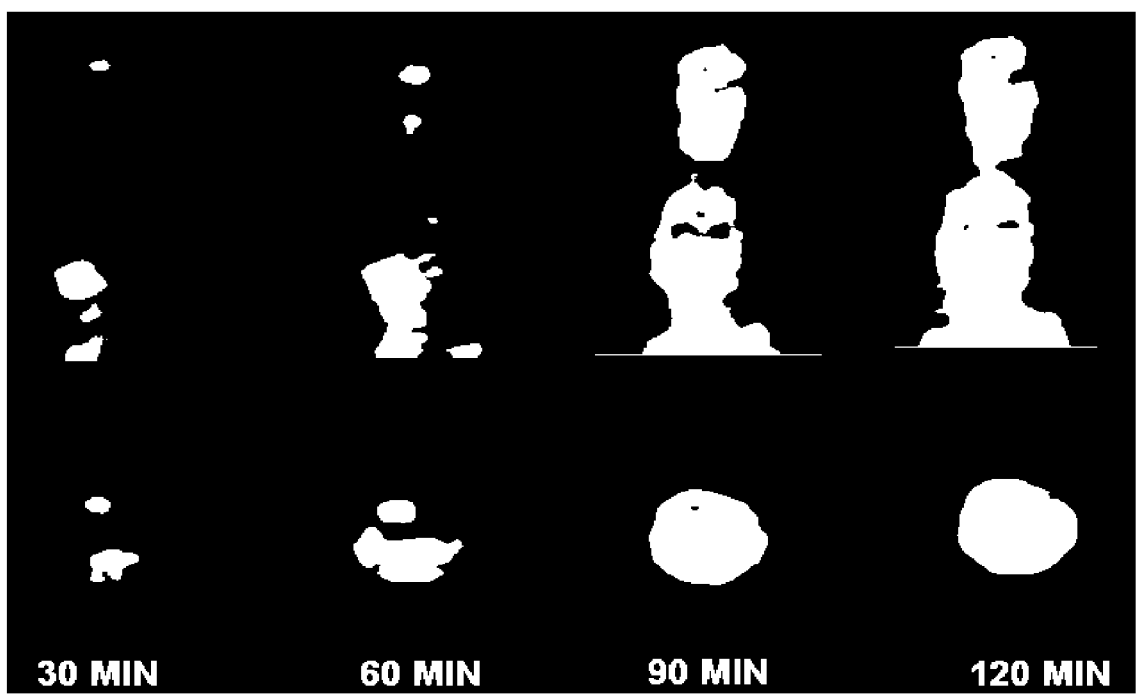
FIG. 4 is the PET imaging of left-brain F98 rat glioma implanted Fischer344 rat after inject L-[$^{18}$F]FET at 30, 60, 90 and 120 minutes respectively; upper row represent the coronal scan and lower row represent the cross section scan.

(6) Commence PET and microPET imaging. Perform image processing after reconstruction of acquired image data; the coronal and cross section scans show in FIGS. 3 and 9. Rat injected L-[$^{18}$F]FET has significant radioactivity accumulation in brain tumor and reach maximum uptake after 90 minutes of injection. In contrast to tumor site, normal tissue have lower radioactivity accumulation of L-[$^{18}$F]FET because of lower amino acid requirement. PET imaging of L-[$^{18}$F]FET shows the definite location of tumor; this finding is totally consistent with the result of biological distribution, i.e., the accumulation of L-[$^{18}$F]FET and tumor-to-normal brain ratio of brain tumor is much higher than that of normal organs except pancreas.

What is claimed is:

1. A method for producing O-(2-[$^{18}$F]fluoroethyl)-L-Tyrosine, comprising:
   using a precursor of formula 1 as a starting material, and
   reacting the starting material using Kryptofix 2.2.2 as a catalyst with $^{18}$F-radioisotope,

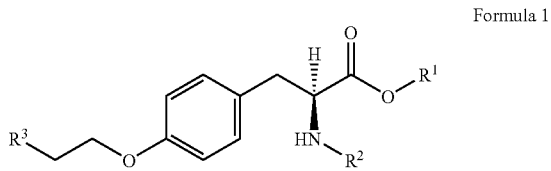

Formula 1 wherein
   $R^1$ is a protective group for the carboxyl functional group and represents an arylalkyl group;
   $R^2$ is a protective group for the amino group and represents a carboxyl group; and
   $R^3$ acts as a leaving group and represents a p-tosyloxy, methane sulfonyloxy or trifluoromethane sulfonyloxy or bromine.

2. The method according to claim 1, further comprising: using silica gel column for purification.

* * * * *